(12) United States Patent
Ronaes et al.

(10) Patent No.: US 9,007,580 B2
(45) Date of Patent: *Apr. 14, 2015

(54) METHOD AND APPARATUS FOR MEASURING PARTICLE SIZE DISTRIBUTION IN DRILLING FLUID

(71) Applicants: Egil Ronaes, Hundaag (NO); Michael A. Freeman, Kingwood, TX (US)

(72) Inventors: Egil Ronaes, Hundaag (NO); Michael A. Freeman, Kingwood, TX (US)

(73) Assignee: Schlumberger Norge AS, Tananger (NO)

( * ) Notice: Subject to any disclaimer, the term of this patent is extended or adjusted under 35 U.S.C. 154(b) by 204 days.

This patent is subject to a terminal disclaimer.

(21) Appl. No.: 13/868,039

(22) Filed: Apr. 22, 2013

(65) Prior Publication Data

US 2014/0146314 A1 May 29, 2014

Related U.S. Application Data

(63) Continuation of application No. 13/123,541, filed on Apr. 11, 2011, now Pat. No. 8,427,640.

(51) Int. Cl.
G01N 15/02 (2006.01)
G01N 15/14 (2006.01)
E21B 47/00 (2012.01)
E21B 21/08 (2006.01)
G01N 15/00 (2006.01)

(52) U.S. Cl.
CPC .... *G01N 15/1459* (2013.01); *G01N 2015/0053* (2013.01); *E21B 47/00* (2013.01); *E21B 21/08* (2013.01)

(58) Field of Classification Search
None
See application file for complete search history.

(56) References Cited

U.S. PATENT DOCUMENTS

| 4,728,190 A | 3/1988 | Knollenberg |
| 4,917,496 A | 4/1990 | Sommer |
| 5,043,591 A | 8/1991 | Ludlow et al. |
| 2006/0274309 A1 | 12/2006 | Cerni et al. |

FOREIGN PATENT DOCUMENTS

| KR | 20020021808 A | 3/2002 |
| KR | 200300083321 A | 10/2003 |

OTHER PUBLICATIONS

International Search Report and Written Opinion issued in PCT/US2009/061471 on May 28, 2010, 12 pages.
Office Action issued in EA201170599 on Feb. 11, 2013, 4 pages.
Examination Report issued in CA2,740,587 on May 9, 2013, 2 pages.
Mettler Toledo, Lansentec D600 Hardware Manual, 003-15011 Rev H , Mettler-Toledo AutoChem, Inc., Redmond, WA, Feb. 2004, 80 pages.

*Primary Examiner* — Kara E Geisel
*Assistant Examiner* — Amanda Merlino (57) ABSTRACT

A method includes determining particle size distribution (PSD) in a fluid flow line based on a range of sizes for at least one particle in the fluid flow line and duration of reflection of a laser beam from the at least one particle. The laser beam is focused from a laser beam instrument in direct contact with the fluid low line.

18 Claims, 6 Drawing Sheets

METHOD AND APPARATUS FOR MEASURING PARTICLE SIZE DISTRIBUTION IN DRILLING FLUID

CROSS REFERENCE TO RELATED APPLICATIONS

This application is a continuation of U.S. application Ser. No. 13/123,541 filed on Apr. 11, 2011 the contents of which are incorporated herein by reference.

BACKGROUND

As oil producing fields are gradually becoming more mature, requests for more advance drilling techniques and equipment to handle the depleted reservoirs are becoming more common. For example, older, more mature oil reservoirs may include fractures in the drilled walls of the well bore. There are gas fields where production was started while the development of the field was still ongoing. In such fields, depletion due to production and the fact that pressure depleted at a slightly higher rate than expected, resulted in a reservoir that is more easily fractured. Managed pressure drilling (MPD) is an example of advanced tools and equipment that focuses on preventative treatment of induced and natural fractures in the drilled well bore. Further, to continue to produce from the reservoir, the fractures are bridged using various types of bridging material.

There is also a growing demand within the industry to find equipment that can run real time measurements of particle size distribution to improve control of physical conditions within a reservoir with addition of lost circulation material (LCM) and to maintain this optimized particle concentration and thereby prevent losses. Typically, particle size distribution (PSD) is measured on a sample of a wellbore fluid for which PSD is being determined. That is, a sample of drilling fluid is taken out of the flow line and the PSD of the sample is determined.

Conventional processes and/or equipment for determining PSD employ laser diffraction methods to determine the PSD of the sample. Laser diffraction based particle size analysis relies on the fact that particles passing through a laser beam will scatter light at an angle that is directly related to their size. This method typically assumes that all particles are spherical regardless of actual shape of the particles. As particle size decreases, the observed scattering angle increases logarithmically. Scattering intensity is also dependent on particle size, diminishing with particle volume. Large particles therefore scatter light at narrow angles with high intensity whereas small particles scatter at wider angles but with low intensity. In laser diffraction, particle size distributions are calculated by comparing the sample's scattering pattern with an appropriate optical model by exploiting the above-described behavior of the particles that pass through the laser beam. Further, with laser diffraction, normalized values of particle size distribution are reported. In a normalized system, changes in one area may change the distribution in other regions completely.

Often times, sampling of the fluid in the flow line leads to inaccuracy in the PSD measurement of materials in the fluid, because the sample is often diluted in order to use laser diffraction methods to determine PSD. Dilution of the sample often breaks up conglomerated particles, thereby altering the sample before PSD measurements are taken. Therefore, the PSD of the sample may not be an accurate representation of the PSD of the flow line.

SUMMARY

In general, in one aspect, the invention relates to a method for measuring particle size distribution in a fluid material, inserting a laser beam instrument directly in the fluid flow line, wherein the laser beam instrument focuses a laser beam on a window directly coupled with the fluid flow line, wherein the fluid flow line comprises a fluid having a plurality of particles of different sizes, measuring a diameter of at least one particle in the fluid flow line by reflectance of the at least one particle as the at least one particle passes through the focused laser beam, determining a duration of reflection of the at least one particle, and obtaining a count of particles in each of a pre-set range group of particle sizes, wherein the count of particles is used to determine particle size distribution in the fluid flow line.

In general, in one aspect, the invention relates to An apparatus for determining particle size distribution, comprising a laser beam instrument comprising a window and a laser light source configured to focus a laser beam in the window, wherein the window is directly coupled with a fluid flow line comprising a fluid having a plurality of particles disposed therein, and an optics configured to rotate circularly to focus the laser beam on the window, wherein a diameter of each of the plurality of particles is measured by reflectance of the plurality of particles as the plurality of particles pass through the focused laser beam, wherein the measured diameter of each of the plurality of particles is used to determine a count of particles for each of a pre-set range group of particles, wherein the count of particles of each pre-set range group of particles is used to determine particle size distribution of the fluid flow line.

Other aspects of the invention will be apparent from the following description and the appended claims.

DETAILED DESCRIPTION

Specific embodiments disclosed herein will now be described in detail with reference to the accompanying figures. Like elements in the various figures are denoted by like reference numerals for consistency.

In the following detailed description of embodiments disclosed herein, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments disclosed herein provide a method and apparatus for measuring particle size distribution in a drilling fluid flow line. More specifically, embodiments disclosed herein relate to laser-based reflectance measurements for evaluation of particle size distribution for bridging of formation pores and fractures in an oil reservoir.

Figure 1:
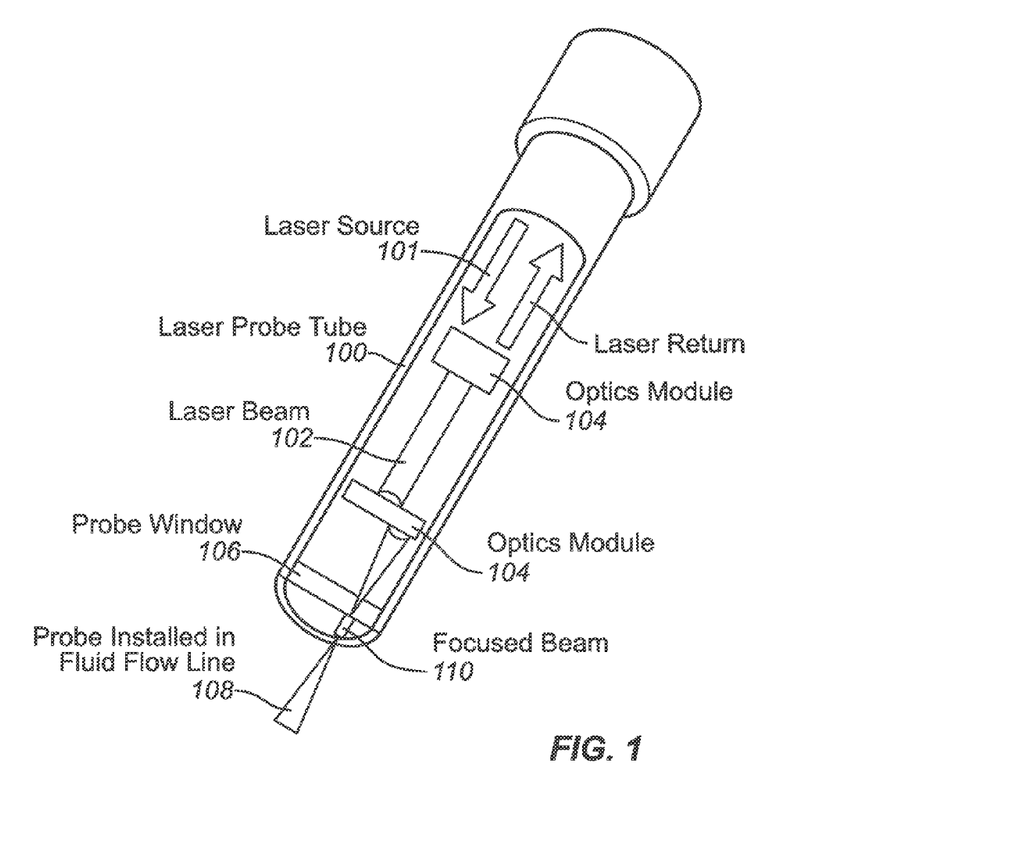
FIG. 1 shows a beam reflectance instrument in accordance with one or more embodiments disclosed herein.

FIG. 1 shows a laser beam instrument in accordance with one or more embodiments disclosed herein. The laser beam instrument includes a laser beam (102), optics (104), and a probe window (106).

The laser beam instrument is a probe tube (100) that includes a laser beam (102). The laser beam (102) is generated from a solid-state laser light source (101) that provides a continuous beam of monochromatic light that is launched down the laser probe (100). Those skilled in the art will appreciate that the light source may be any light source capable of generating a laser beam. An intricate set of lenses (i.e., optics (104)) focuses the laser light to a small spot on the surface of the probe window (106). This focal spot is carefully calibrated to be positioned at the interface between the probe window and the actual process. Tightly controlling the position of the focal spot is necessary for a sensitive and repeatable measurement. A precision motor (not shown) (e.g., a pneumatic or an electric motor) is used to rotate the precision optics (104) in a circular motion at a constant speed. The rotating optics act to split the laser beam (102) into a circle rotating with an alternating speed between 2 and 4 m/s. The speed is carefully monitored and controlled throughout the measurement to ensure maximum precision in the data. In one or more embodiments disclosed herein, standard probes operate to provide a fixed scan speed between 1 and 4 m/s. Preferably, in one or more embodiments, the scan speed is 2 m/s for finer particles and 4 m/s for coarse particles. In the laser beam instrument, there may be a mechanical switch that allows for toggling between 2 and 4 m/s, using only those two positions. Those skilled in the art will appreciate that some models are capable of faster scan speeds and may be calibrated to allow operation at different speeds to improve performance in particular applications.

The focused beam (110) scans a circular path at the interface between the probe window (106) and the fluid flow line (108). As the scanning focused beam (110) sweeps across the face of the probe window (106), individual particles or particle structures backscatter the laser light back to the probe tube (100). Particles and droplets closest to the probe window (106) are located in the scanning focused spot and backscatter distinct pulses of reflected light. That is, the backscattered light is detected by the probe tube (100) as a pulse measured from one edge of the particle to the opposite edge of the particle.

Figure 2:
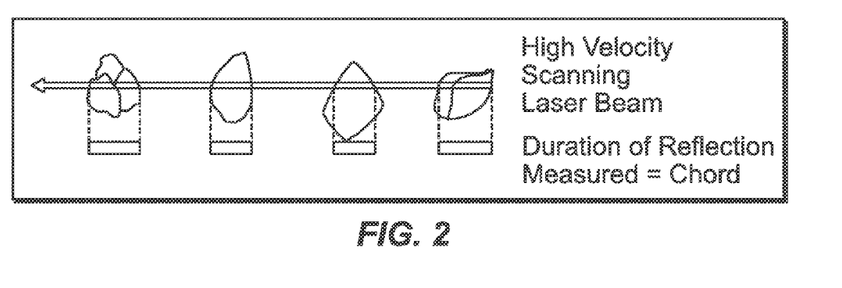
FIG. 2 shows a chord length of a particle in accordance with one or more embodiments disclosed herein.

The pulses of backscattered light are detected by the probe (100) and translated into chord lengths based on the a calculation of the scan speed (velocity) multiplied by the pulse width (time). A chord length is simply defined as the straight-line distance from one edge of a particle or particle structure to another edge (i.e., the diameter of a particle). FIG. 2 shows a chord length calculation in accordance with one or more embodiments disclosed herein. Specifically, FIG. 2 shows a high velocity scanning laser beam that scans across the diameter of each particle that reflects off the laser beam. The duration of reflection measured is a chord. Thousands of individual chord lengths are typically measured each second to produce a "chord length distribution", which shows the number of individual chords measured per second (y-axis) as a function of the chord length dimension (x-axis). The chord length distribution, as a "fingerprint" of the particle system, provides the ability to detect and monitor changes in particle dimension and particle count in real time. In one or more embodiments, the laser beam instrument determines the particle size distribution (PSD) of a fluid flow line with an accuracy of 1000-2000 μm.

Those skilled in the art will appreciate that unlike other particle size analysis techniques, the laser beam instrument disclosed herein makes no assumption of particle shape. This allows the fundamental measurement to be used to directly track changes in the particle system without unnecessary complex mathematical assumptions that could introduce significant errors to the measurement.

In one or more embodiments disclosed herein, the laser beam instrument may be a Lasentec® FBRM® (Focused Beam Reflection Measurement) instrument, commercially available from METTLER TOLEDO (Columbus, Ohio). Further, in one or more embodiments disclosed herein, the probe window (106) is a sapphire window.

As described above, the laser beam instrument (probe) described in FIG. 1 is used to measure PSD of particles in a fluid line that provides a wellbore fluid to bridge/plug fractures and pores in a reservoir. More specifically, the bridging material (also known as lost circulation material (LCM)) is added to the fluid flow line and the PSD of the bridging material is calculated using the laser beam instrument described above. Bridging material is a substance added to cement slurries or drilling mud to prevent the loss of cement or mud to the formation and may be fibrous, flaky, or granular material. Bridging materials may include, but are not limited to, Fordadol Z2, G-Seal® (provided by M-I LLC (Houston, Tex.)), Microdol 40/200, Calcium Carbonate M, and/or any combination thereof. In one or more embodiments disclosed herein, an ideal blend of bridging materials (i.e., an ideal packing theory) combines 4-6 bridging products, such as those described above.

Those skilled in the art will appreciate that the laser beam instrument in embodiments disclosed herein is able to provide a continuous measurement of particle sizes and changes in PSD while adding various sized products to a fluid flow line. Thus, the size of the particles that are added does not affect the instrument's ability to detect changes in PSD.

In one or more embodiments disclosed herein, the laser beam instrument is set up (in a training phase) in software before being inserted into the fluid flow line for purposes of obtaining PSD measurements. Table 1 shows an overview of products, planned concentrations, and particle size ranges used in the software setup for the laser beam instrument. The ranges are chosen as typical ranges for characterization of each added bridging material such that the laser beam instrument may identify changes in population of each bridging product as they are added to the fluid flow line. The particle sizes are chosen to cover both pore bridging and bridging of induced or natural fractures while drilling depleted zones in the reservoir.

TABLE 1

| Fracture Bridging Blend | | |
| --- | --- | --- |
| Product | Concentration ($kg/m^3$) | Particle size group range (μm) |
| Fordadol Z2 | 10 | 632-2000 |
| G-Seal ® | 35 | 233-683 |
| Microdol 40/200 | 20 | 47-252 |
| Calcium Carbonate M | 35 | 2-50 |

In one or more embodiments disclosed herein, the PSD measurements obtained by the laser beam instrument are count based rather than based on normalized values. Thus, advantageously, the count based interpretation allows for each channel in the system to be independent of changes in other regions of the distribution. In one or more embodiments disclosed herein, the measured particles may be grouped into the different ranges shown in Table 1 in the laser beam instrument software and report form. This enables offshore personnel to maintain the concentration of the different bridging materials in the rig inventory according to actual changes in particle size distribution.

Figure 3:
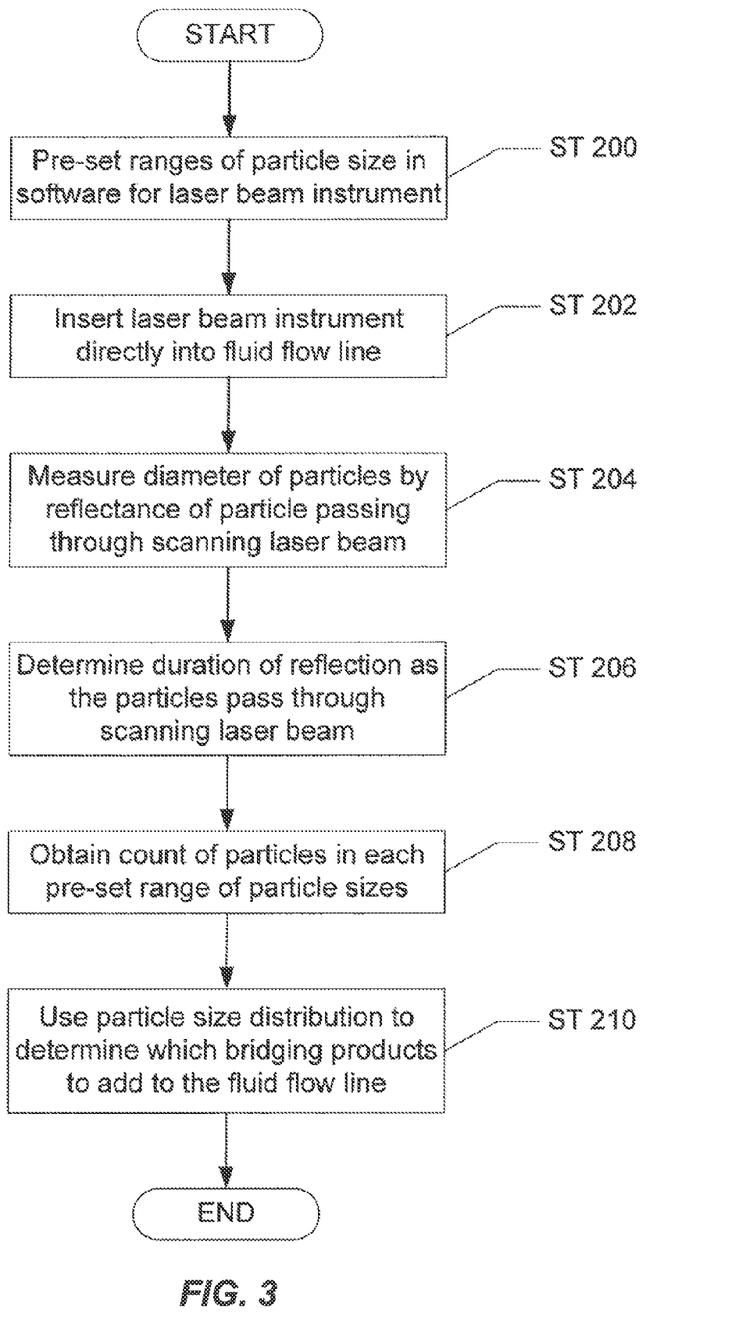
FIG. 3 shows a flow chart in accordance with one or more embodiments disclosed herein.

FIG. 3 shows a flow chart in accordance with one or more embodiments of the present disclosure. Initially, software values for the concentrations and particle size groups for various LCM/bridging materials are pre-set in the laser beam instrument (ST 200). In addition, the scanning speed is set both in hardware and software, and determines what size range may be detected by the instrument. For example, a scanning speed of 4 m/s is applicable for sizes 2-2048 μmm. In one or more embodiments disclosed herein, the laser beam instrument may be toggled between a scanning speed of 2 and 4 m/s. The scanning speed is set by the rotational speed of the optics module, which is pneumatically driven. Subsequently, the probe tube including the laser beam instrument is inserted directly into the fluid flow line (ST 202). More specifically, the probe window of the laser beam instrument is placed directly into the particle system (the fluid flow line). The probe tube may also be inserted into a return line of drilling fluid, where the return line includes drilling fluid traveling upward to the surface; thus, embodiments disclosed herein are not limited to a laser beam instrument that is inserted only into a flow line. In one or more embodiments, the probe tube is inserted into a turbulent well-mixed fluid flow line at an angle between 30 and 60 degrees. Preferably, in one or more embodiments, the laser beam instrument is inserted at a 45 degree angle into the fluid flow line. Next, a measurement of the diameter or chord length of particles is obtained using the reflectance of particles passing through scanning laser beam (ST 204).

Continuing with FIG. 3, the duration of the reflection of the particles is determined (ST 206). The method of measurement is based on the duration of reflection as the particles pass through the high velocity scanning laser beam. The duration of reflection measured provides the chord length of each particle, as discussed above. Thus, the measurements depend on the shape of the particles and the orientation of the particles as the measurement is actually registered. The high number of measurements (typically 50000-200000 particles/second), despite the particle shape, ensures a robust representation of the actual particles. Thus, a measure of the diameter of the particles over a specific time interval (e.g., 30 seconds) provides the average count of particles in each pre-set group of particle sizes. This calculation is subsequently performed to obtain the count of particles in each particle size group range (ST 208). Finally, the particle size count for each particle size group is used to determine what blend of bridging materials to add to the fluid flow line to bridge pores and fractures in the reservoir (ST 210). The particle size count is also used to determine the required minimum particle concentration necessary to identify changes in PSD due to additions of particles.

Using the method described above, the probe instrument measures changes in particle sizes for each individual addition of particles into the drilling fluid, regardless of the size of the particles that are added to the flow line. In other words, PSD is used to determine the blend of particles of bridging materials that is needed to plug pores and fractures in a reservoir. The PSD measurements may also be used to determine the effectiveness and verify the bridging effect of a blend of bridging products that is added to the fluid flow line. In one or more embodiments, the PSD measurements may also be used to determine how much material for preventing fractures in the reservoir is needed. The preventative materials can also be added to the flow line in a manner similar to the bridging materials that are used to plug existing fractures and pores. Further, in addition to being used to bridge and prevent pores and fractures, in one or more embodiments disclosed herein, PSD measurements may also be used to replace measurement of NTUs (Nephelometric Turbidity Units). Turbidity refers to how 'cloudy' a fluid is, and an NTU is a measurement unit that measures the lack of clarity of water, which could also be affected by the particle size distribution.

In one or more embodiments disclosed herein, the laser beam instrument includes a fine mode and a coarse mode. The coarse mode allows the instrument to interpret particles with very rough edges or even agglomerates as one particle. The course mode is a signal filter applied to the data before turning the data into chord lengths. This is useful for the characterization of large particles in the presence of many small particles. Fine mode is more sensitive than coarse mode, and is used to identify small particles. In one or more embodiments, fine mode is the default mode.

FIGS. 4-7 show data review screens of the laser beam instrument in accordance with embodiments of the present disclosure during various examples of circulating fluid and adding a one or more bridging material(s) to the fluid. Each figure is described in more detail below.

Figure 4:
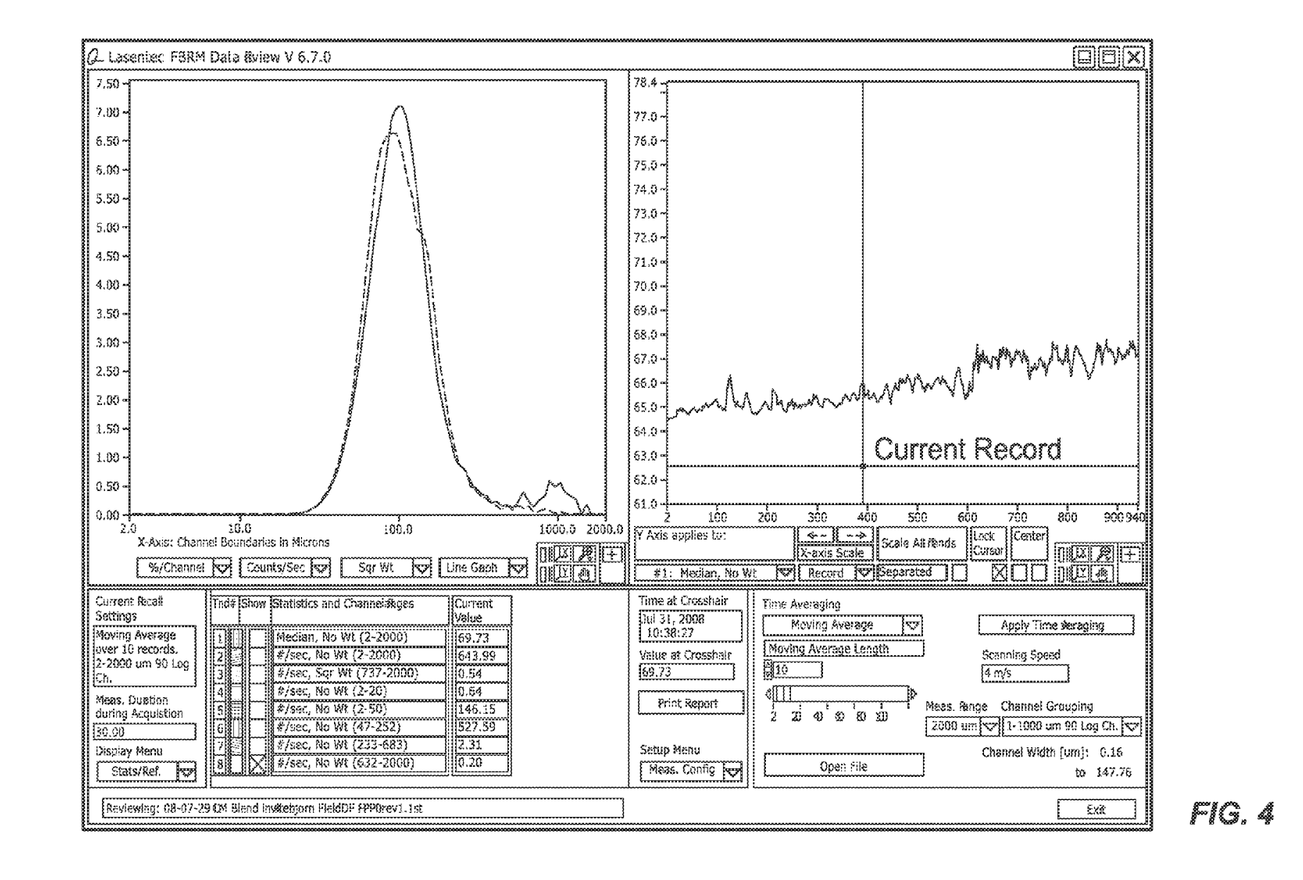
FIGS. 4-7 show data review screens for measuring particle size distribution in accordance with one or more embodiments disclosed herein.

FIG. 4 shows a data review screen for the addition of Fordadol Z2 bridging product in accordance with one or more embodiments disclosed herein. More specifically, FIG. 4 shows the data review screen while circulating and conditioning the fluid before product addition for bridging fractures and pores is added. The left window shows the PSD of the fluid while circulating. The crosshair in the right side window shows a graph of particle size distribution a short while after the addition of 10 g/l Fordadol Z2 with a D50>1000 μm. The laser beam instrument measures the change in particle counts between 632 and 2000 μm, which is the pre-set range in the software to identify the Fordadol Z2 product. The curve in the right window demonstrates that the particle count shows a steady increase after the addition of the product completes. This increase may be because some particle agglomerates are larger than the instruments maximum readable size of 2000 μm and the counts increase over time as these large agglomerates disperse.

Figure 5:
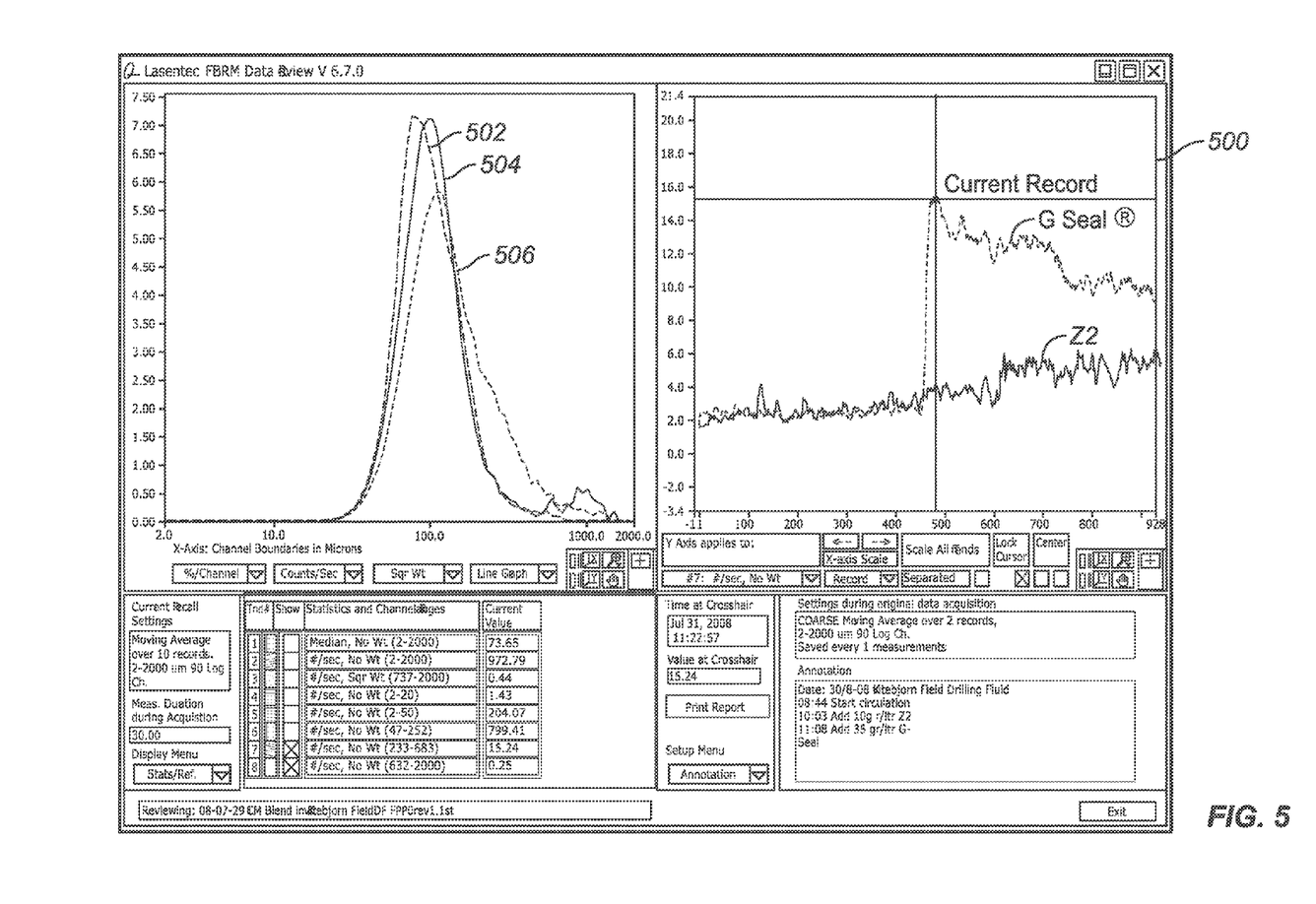

FIG. 5 shows changes in the PSD measured by the laser beam instrument due to the addition of G-Seal® bridging product. The curve in the right hand window shows a sharp increase (500) in particle counts immediately after addition of 35 g/l G-Seal®. Those skilled in the art will appreciate that the amount of G-Seal® added to the fluid flow line may be any amount, and that 35 g/l is merely an example. The decreased particle count after the initial peak is due to attrition effect as the particles are reduced in size mechanically. The change may also be caused by aggregates that disperse over the first few circulations in the fluid flow loop before the fluid reaches a homogenous condition. A first curve (502) in the left hand size window describes PSD before any addition of particles from bridging materials. A second curve (504) shows PSD after addition of Fordadol Z2 and is close to the first curve (502) except for the increase of particles in the 1000 μm range. A third curve (506) describes the expected shift to the right in the size area between 200 and 700 μm following the addition of G-Seal®.

Figure 6:
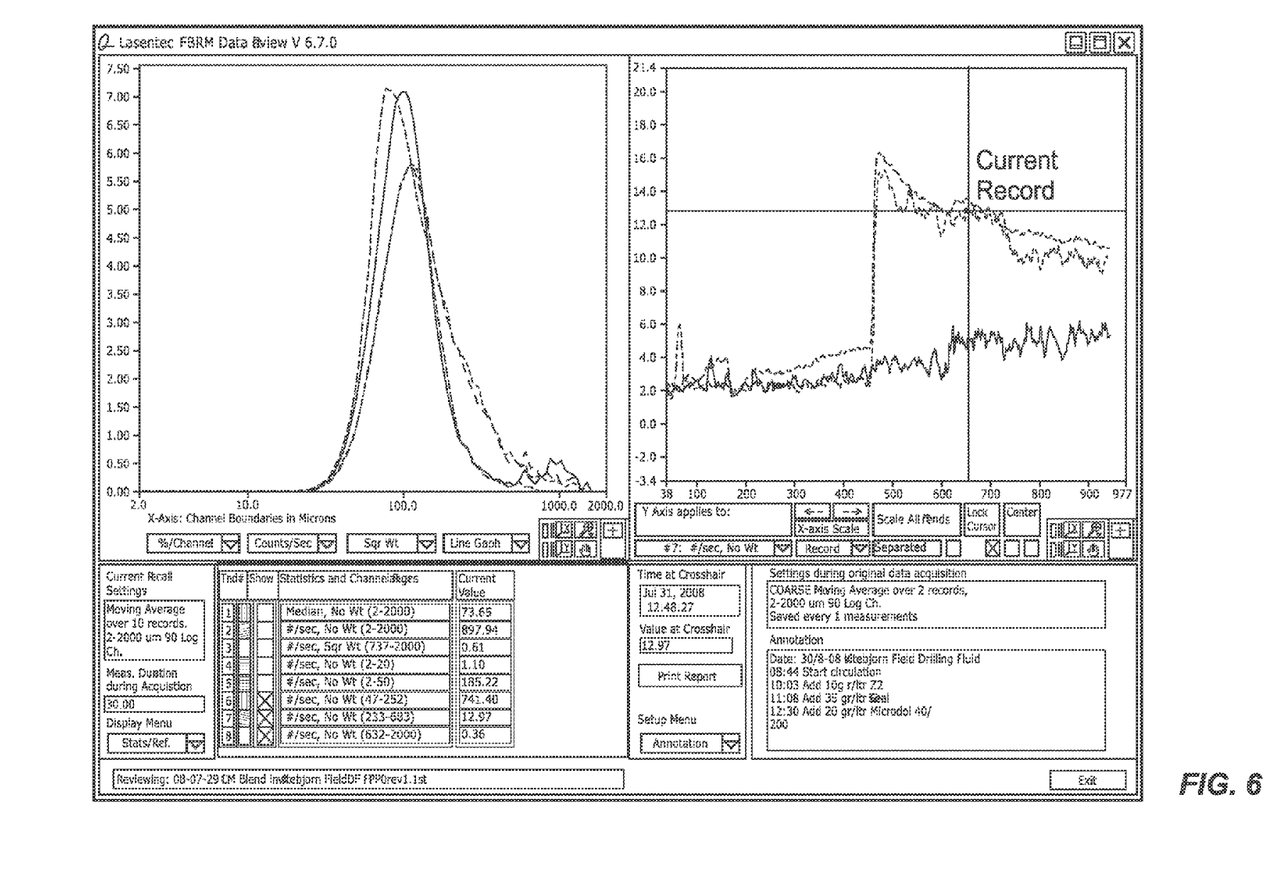

FIG. 6 shows changes in the PSD measured by the laser beam instrument due to the addition of Microdol 40/200 bridging product. The specified size range used to identify Microdol 40/200 that is pre-set into the laser beam instrument using software is 47-252 μm. The addition of Microdol 40/200 shows a similar trend as with the addition of G-Seal® described in FIG. 5. The smaller fraction of G-Seal® falls in line with the coarser fraction of the Microdol 40/200, and thus, is registered by the laser beam instrument in the same manner as the addition of G-Seal®. The higher number of counts of particles between 47 and 252 µm before the addition of Microdol 40/200 indicates that the treated field fluid that was used as a basis to obtain this data review output graph included a certain concentration of particles within this range. The crosshair in the right window is set at the peak immediately after addition of Microdol 40/200.

Figure 7:
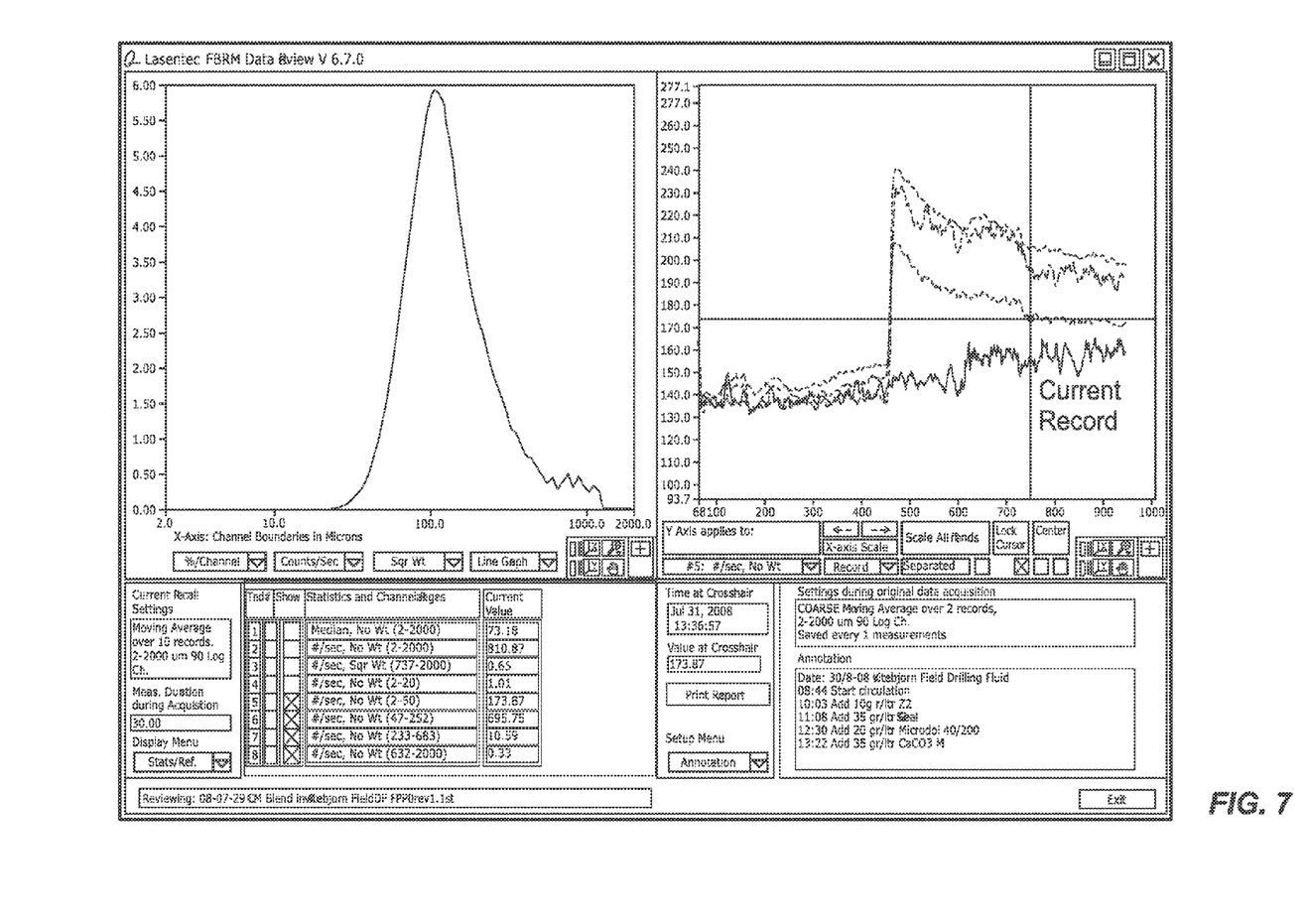

FIG. 7 shows changes in the PSD measured by the laser beam instrument due to the addition of Calcium Carbonate M bridging product. There is no evidenced in FIG. 6 of an increase in counts between 2-50 µm at the cross hair in the right window. This may be due to the relatively high concentration of fine particles present in the fluid before any additions and the finer fraction of the coarser additives. For the data review shown in FIG. 7, the laser beam instrument and software associated with the laser beam instrument are set up to focus primarily on the coarser particles rather than finer particles, which accounts for the graphs shown in FIG. 7.

Embodiments of the disclosure provide a method and apparatus for determining particle size distribution of various materials in a fluid flow line using reflectance of particles in the fluid flow line. Advantageously, the apparatus (laser beam instrument) disclosed herein is inserted directly into the flow line, without having to sample the flow line, resulting in a more accurate determine of the PSD in the flow line. Further, the method of the present disclosure provides an actual count of PSD, rather than normalized values of PSD.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method comprising:
   directly contacting a laser beam instrument with a fluid flow line containing a wellbore fluid;
      determining chord length distribution for at one particle in the fluid flow line;
   determining particle size distribution (PSD) for the at least one particle in the fluid flow line based on the chord length distribution determined; and
   determining bridging effect of bridging material correlating to the PSD, the bridging material to be added to the fluid flow line to bridge a pore or a fracture in a reservoir.

2. The method of claim 1, wherein the laser beam is directed from a laser beam source to a window within the laser beam instrument, the window in communication with the fluid flow line.

3. The method of claim 1, wherein determining the chord length distribution is for a range of sizes for the at least one particle stored in software.

4. The method of claim 1 further comprising:
   monitoring a change in PDS of the fluid flow line to determine a bridging material to be added to the fluid flow line.

5. The method of claim 1 further comprising:
   contacting the laser beam instrument with a return line to determine PSD in the return line containing wellbore fluid.

6. The method of claim 1, wherein determining the PSD for the at least one particle in the fluid flow line is based on changes to the PSD in a fluid flow loop in communication with the fluid flow line.

7. The method of claim 1, wherein the determining PSD further comprises measuring a diameter of the at least one particle over a specified time interval to determine count of the at least one particle.

8. A method comprising:
   receiving a range of sizes for at least one particle in a fluid flow line containing a wellbore fluid;
   inserting a laser beam directly in the fluid flow line;
   detecting pulses of backscattered light from the at least one particle to determine a chord length distribution;
   determining particle size distribution (PSD) in the fluid flow line based on the chord length distribution for the range of sizes for the at least one particle added to the fluid flow line; and
   determining bridging effect of bridging material correlating to the PSD of the at least one particle in the fluid flow line, the bridging material to be added to the fluid flow line to bridge one of a pore and a fracture in a reservoir.

9. The method of claim 8 further comprising:
   monitoring changes to the PSD in a fluid flow loop in communication with the fluid flow line.

10. The method of claim 9 further comprising:
    monitoring changes to the PSD in the fluid flow line to determine the bridging material to add to the fluid flow line.

11. The method of claim 8, wherein the laser beam is directed from a laser beam source to a window within a laser beam instrument, the window coupled to the fluid flow line.

12. The method of claim 11 further comprising:
    rotating optics within the laser beam instrument to focus the laser beam onto the window.

13. A laser beam instrument comprising:
    a laser source to direct a laser beam in contact with at least one particle in a fluid flow line containing a wellbore fluid;
    a fluid flow loop in communication with the fluid flow line; and
    software to receive a range of sizes for the at least one particle in the fluid flow line;
    wherein particle size distribution (PSD) in the fluid flow line and fluid flow loop are determined based on chord length distribution for the range of sizes for the at least one particle received by the software and duration of reflection of the laser beam from the at least one particle,
    wherein a bridging material correlated to the PSD is added to the fluid flow line to bridge one of a pore and a fracture in a reservoir.

14. The instrument of claim 13 further comprising:
    a window to which the laser beam is focused, the window in direct contact with the fluid flow line.

15. The instrument of claim 14, wherein the window is in direct contact with a return line of drilling fluid.

16. The instrument of claim 13 further comprising:
    optics to focus the laser beam onto the window.

17. The instrument of claim 13 further comprising:
    a display for indicating a change in the PDS of the fluid flow line.

18. The instrument of claim 13, wherein the range of sizes for the at least one particle in the fluid flow line is stored in software prior to contacting the laser beam with the at least one particle in the fluid flow line.

* * * * *